(12) United States Patent
Susteric et al.

(10) Patent No.: US 11,272,881 B2
(45) Date of Patent: Mar. 15, 2022

(54) TUBULAR COMPRESSION GARMENT FOR MONITORING THE THERAPY AND PHYSIOLOGICAL ACTIVITY OF A PERSON

(71) Applicant: MESI d.o.o., Ljubljana (SI)

(72) Inventors: Jakob Susteric, Zabukovje (SI); Tomo Krivc, Bohinjska Bistrica (SI)

(73) Assignee: MESI D.O.O., Ljubljana (SI)

( * ) Notice: Subject to any disclaimer, the term of this patent is extended or adjusted under 35 U.S.C. 154(b) by 0 days.

(21) Appl. No.: 17/018,858

(22) Filed: Sep. 11, 2020

(65) Prior Publication Data
US 2021/0068752 A1    Mar. 11, 2021

(30) Foreign Application Priority Data
Sep. 11, 2019    (SI) ................... P-201900171

(51) Int. Cl.
*A61B 5/00*    (2006.01)
(52) U.S. Cl.
CPC .......... *A61B 5/6804* (2013.01); *A61B 5/0004* (2013.01); *A61B 5/0015* (2013.01);
(Continued)
(58) Field of Classification Search
CPC ... A61B 5/0492; A61B 5/0205; A61B 5/6804; A61B 5/0004; A61B 5/0053;
(Continued)

(56) References Cited

U.S. PATENT DOCUMENTS

2014/0276275 A1    9/2014   Stokes et al.
2015/0366504 A1*  12/2015   Connor ............... A61B 5/0492
                                                    600/301
(Continued)

FOREIGN PATENT DOCUMENTS

EP    3501377 A1    6/2019

*Primary Examiner* — Patrick Fernandes
(74) *Attorney, Agent, or Firm* — The Watson IP Group, PLC; Jovan N. Jovanovic (57) ABSTRACT

The object of the invention is a tubular compression garment for monitoring the therapy and physiological activity of the wearer, which belongs to the field of medical devices and can be used, among other things, for the treatment or alleviation of symptoms of various diseases, preferably for the treatment or alleviation of symptoms of venous vasculature in the legs. A tubular compression garment for monitoring the therapy and physiological activity of the person comprises a classic tubular compression garment (20) with an attached stretch-measuring sensor (10) and a sensor-control unit (6) with contacts (4, 11, 12) for connection to the stretch-measuring sensor (10), wherein the sensor-control unit (6) further comprises a motion sensor, a photoplethysmographic sensor, a temperature sensor, and a processing unit with a clock; and wherein a sensor-control unit (6) is detachably secured to the compression garment (20). The sensor-control unit (6) processes the data obtained from the sensors or by real-time calculation, and saves it to the local memory or transmits it simultaneously or occasionally through the communication unit to an external device equipped with a dedicated application that enables the data to be monitored, stored, processed or forwarded.

11 Claims, 4 Drawing Sheets

(52) U.S. Cl.
CPC .......... *A61B 5/0053* (2013.01); *A61B 5/6828* (2013.01); *A61B 2560/0214* (2013.01); *A61B 2562/0271* (2013.01)

(58) Field of Classification Search
CPC .......... A61B 5/6828; A61B 2560/0214; A61B 2562/0271; G06K 9/00342; G06K 9/00335
See application file for complete search history.

(56) References Cited

U.S. PATENT DOCUMENTS

| | | |
|---|---|---|
| 2016/0066821 A1 | 3/2016 | Mestrovic et al. |
| 2016/0135516 A1 | 5/2016 | Cobbett et al. |
| 2016/0242646 A1* | 8/2016 | Obma .................. A61B 5/0024 |
| 2017/0036066 A1* | 2/2017 | Chahine ............. G06K 9/00342 |
| 2018/0199635 A1* | 7/2018 | Longinotti-Buitoni ...................... A61B 5/0205 |
| 2018/0249957 A1 | 9/2018 | Bay |

* cited by examiner

TUBULAR COMPRESSION GARMENT FOR MONITORING THE THERAPY AND PHYSIOLOGICAL ACTIVITY OF A PERSON

1 DESCRIPTION OF THE INVENTION

1.1 Object of the Invention

The object of the invention is a tubular compression garment for monitoring the therapy and physiological activity of the wearer, which belongs to the field of medical devices and can be used, among other things, for the treatment or alleviation of symptoms of various medical conditions, preferably for the treatment or alleviation of symptoms of venous vasculature in the legs, including chronic venous disease (CVD) in all its stages. The tubular compression garment for monitoring the therapy and physiological activity of the person comprises a classic tubular compression garment with an attached stretch-measuring sensor and a sensor/control unit with contacts for connection to the stretch-measuring sensor, wherein the sensor/control unit further includes a motion sensor, a photoplethysmographic sensor and a temperature sensor, and where the detachable sensor/control unit can be attached to the garment.

1.2 State of the Art

The term "classic tubular compression garment", hereinafter referred to as "garment", refers to tubular compression garments which are the state of the art. They are made of elastic materials, have a predetermined degree of compression based on the degree of elasticity of the material, and are manufactured in different sizes. In the case of compression socks, the predetermined degree of compression is usually 15 to 30 mmHg, but may also exceed 50 mmHg; for compression garments for the arms, the degree of compression is usually 5 to 10 mmHg; and for compression shirts, the degree of compression is usually 2 to 5 mmHg. A compression garment can be made from one piece as a tubular element, or it can be made in the form of a jacket with fasteners, usually Velcro straps, with which the garment is fastened, and where by adjusting the Velcro straps, the degree of compression can be adjusted. Classic compression garments do not allow for obtaining and providing real information on whether the person followed the doctors instructions, i.e. whether the person wore the compression garment and for how long, what physical activity he/she engaged in while wearing the compression garment, or whether changing the compression garment is required depending on the duration of the wear, as the elasticity of the material from which the compression garments are made decreases with regular wear, and thus the required degree of compression is no longer guaranteed.

The U.S. patent application no. US20150297100A1 presents a sock for measuring the physiological activity of the person, primarily his/her blood pressure, which can be used to alert to potential health issues of the user in a timely manner. The sock has a ring attached to the top, along its entire circumference, which houses a blood pressure sensor with a button for sensor activation, a display screen for measurements, and a communication unit for transmitting data to an external device. The sock is made up entirely of materials that have a high electrical conductivity, such as silver or copper yarn, wherein said materials allow for changing the compression of the sock while being worn. For this purpose, the ring is fitted with two control buttons, whereby pressing the first control button increases the compressive force to the user's leg and the second control button reduces the compressive force to the leg; however, the application does not reveal in what manner the increase or decrease in compressive force is performed. The sock presented in the said application requires the use of specific expensive materials and does not allow for monitoring of the patient's treatment.

The U.S. patent application no. US20170079868A1 presents a compression system for the treatment of venous leg ulcers. It is comprised of two elastic layers, namely a "sleeve", i.e. a sock representing the inner layer with a predetermined degree of compression, and a bandage that represents the outer layer, wherein the bandage has colour indicators to indicate the final degree of compression of the system, and wrapping the bandage around the inner layer controls the pressure by which the bandage presses on the inner layer, thereby controlling the final degree of compression of the compression system on individual parts of the leg. The compression system ensures that the compression on the limb stays within the prescribed limits over the course of several days of treatment, including during the patients activity. The following describes a sensor for measuring the degree of compression, the sensor being made of electro-conductive yarn woven into the fabric from which the sock is made. The said system allows setting the required compression when applied to the patients limb, but does not allow for obtaining and providing real information about whether the patient followed the doctors instructions, i.e. whether he/she wore the compression sock and for how long, what was the patient's physical activity while wearing the compression sock, and how the patient's activity affects change.

A technical problem that is not satisfactorily resolved is the direct and real-time monitoring of whether the patient is following the prescribed treatment therapy, since non-compliance with the doctors instructions for wearing is one of the major problems associated with the treatment using compression garments. In addition, the measured values recorded by the sensor unit can be used to determine how different physical activities of the patient affect the course of the treatment, and the therapy may be adjusted accordingly.

1.3 Description of the Invention

According to the invention, the task is solved by a tubular compression garment for monitoring the therapy and physiological activity of the person, which, through an attached stretch-measuring sensor and a sensor/control unit, actively monitors whether the patient uses the compression garment, his/her activity, physiological parameters and/or the course of treatment of the patient wearing the compression garment. The stretch-measuring sensor is preferably attached to the compression garment in such a way that it measures the stretch of the garment especially in the circumferential direction, perpendicular to the longitudinal axis of the body part which the compression garment embraces, hereinafter referred to as "circumferential direction".

The compression garment, according to the invention provides the patient, i.e. the person wearing the compression sock, and the doctor an insight into the quality of the therapy and thus contributes to a more effective treatment. In addition the compression garment according to the invention provides real-time information on whether—according to the patients indication and his/her physical activity—the correct degree of compression is being used, for how long the patient wears the garment and during what types of physical activity; the stretch-measuring sensor monitors how the circumference of the body part wrapped by the compression garment changes and thus the current pressure of the compression garment on that part of the body, i.e. the current degree of compression, whether during different physical activities of the patient or due to other problems that may affect that part of the body, when it is necessary to replace the compression garment due to regular wear, since regular wear reduces the elasticity of the material from which the compression garments are made and the required degree of compression is no longer guaranteed. The stretch-measuring sensor provides time-based detection of any changes in that part of the body, such as swelling of the legs, based on the current state of the person, thus allowing for adapting the therapy. For example, real-time measuring of stretch, which can be compared to movement at a given moment or heart rate at a certain point in time, provides information on the type of activity when the swelling of the legs changed or what the heart rate was when it occurred.

Hereinafter an embodiment of the tubular compression garment for the leg according to the invention is described, i.e. a compression sock, without however limiting the extent of protection which applies to all tubular compression garments.

The compression sock according to the invention is described below and presented in the following figures:

FIG. 4 shows an embodiment of a usage flowchart The compression sock for monitoring the therapy and physiological activity of the person, shown in FIGS. 1 and 2 comprises a classic compression sock 20, hereinafter referred to as "a sock", comprising at least one stretch-measuring sensor 10, which is attached to the sock 20, and a sensor/control unit 6 which is detachably secured to the sock 20, wherein the sock 20 is provided with a socket 9 for receiving the sensor-control unit 6, the socket 9 is provided with first contacts 11 for connecting to the stretch-measuring sensor 10, the sock 20 is provided with a hole 7 in the area of the socket 9, and the sensor-control unit 6 is provided with second contacts 4 to connect to the first contacts 11 made on the socket 9, and the sensor/control unit 6 includes at least a motion sensor, a photoplethysmographic sensor and a temperature sensor. The stretch-measuring sensor 10 is preferably attached to the sock 20 in such a way that it measures the stretch of the sock especially in the circumferential direction.

Figure 1:
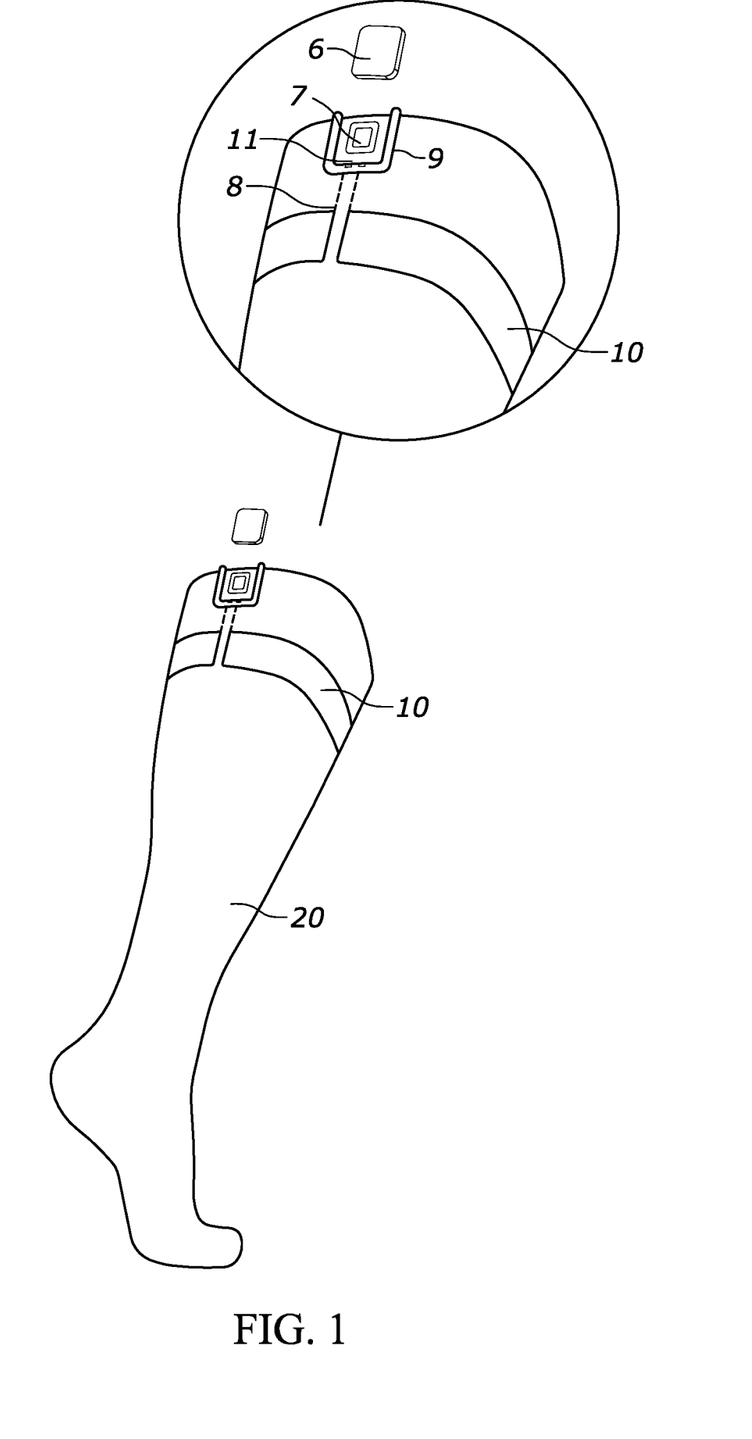
FIG. 1 shows the first embodiment of the compression sock with a single attached sensor for measuring stretch
Figure 2:
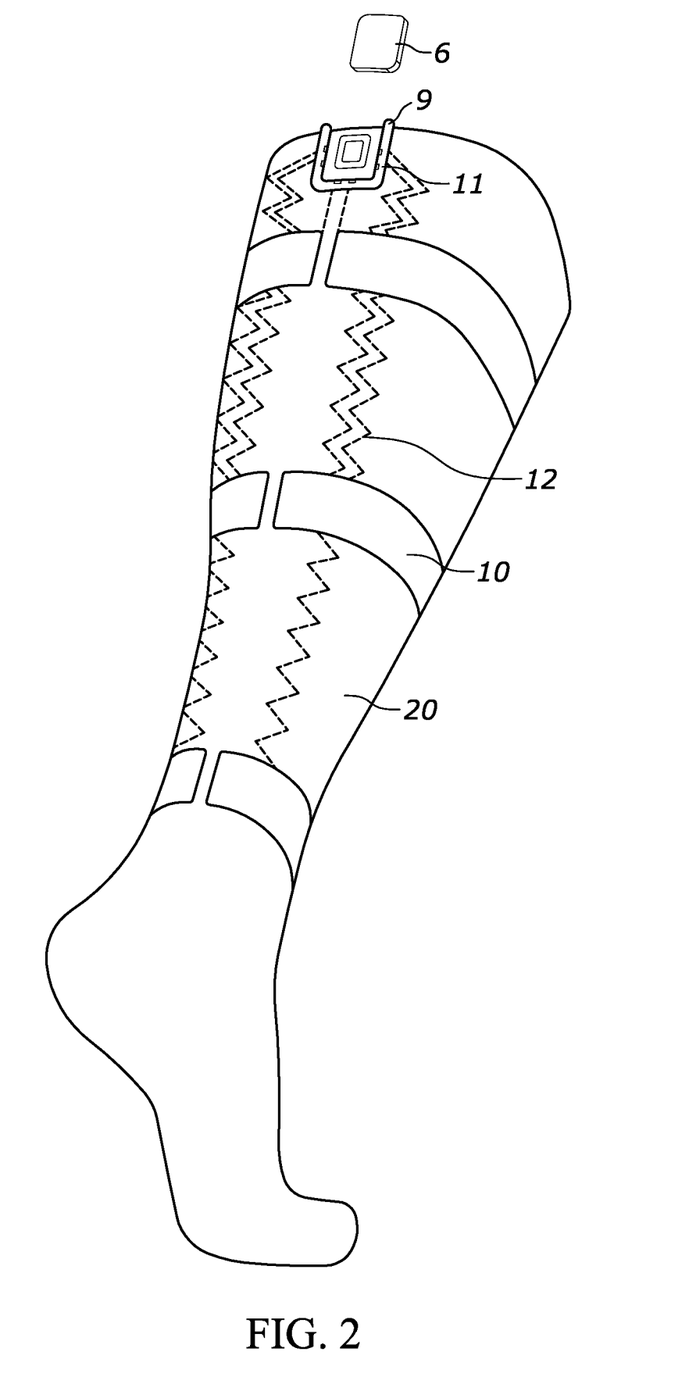
FIG. 2 shows the second embodiment of the compression sock with three attached sensors for measuring stretch

The sock 20 has a silicone print on the upper inner edge that prevents the sock from sliding off the leg during wear.

The sock 20 has at least one stretch-measuring sensor 10 attached in the direction that is essentially perpendicular to the users leg when standing while wearing the sock 20. The stretch-measuring sensor 10 is implemented as a strip made of electroactive polymers that change their capacitance with stretch. Suitable strips made of electroactive polymers are, for example, DuPont Intexar Health, StretchSense StretchFABRIC, Parker Hannifin FlexSense, etc. The attachment of the sensor/strip 10 to the sock 20 is accomplished in known ways, for example by sewing, ultrasonic welding, thermal welding or gluing with a specially assigned adhesive.

The attachment point of the stretch-measuring sensor 10 and the length of the stretch-measuring sensor 10 are chosen to provide as accurate measurements as possible of the change in stretch. The length of the stretch-measuring sensor 10, i.e. the length of the strip of electroactive polymers is, therefore, at least equal to one third of the circumference of the sock 20 at the attachment point of the sensor 10, and such that, at a maximum, a distance of at least 5 mm is guaranteed between both ends of the stretch-measuring sensor 10.

In the preferred embodiment shown in FIG. 1, the sock 20 has a stretch-measuring sensor 10 attached in one place—i.e. below the knee in the upper region of the calf, where the circumference of the lower leg is the largest—wherein the length of the stretch-measuring sensor is such that, at a maximum, a distance of at least 5 mm is still guaranteed between both ends of the stretch-measuring sensor 10. The larger the area covered by the stretch-measuring sensor 10, the more accurate the measurement can be, as changes occur over a larger area.

In the second embodiment shown in FIG. 2, the sock 20 has a stretch-measuring sensor 10 attached in three places—i.e. below the knee in the upper calf area, in the middle-calf area and in the ankle area—wherein the length of each stretch-measuring sensor 10 is such that, at a maximum, a distance of at least 5 mm is still guaranteed between both ends of the stretch-measuring sensor 10.

The connection of the stretch-measuring sensor 10, i.e. the two ends of the strip of electroactive polymers, to the first contacts 11 provided on the socket 9 is accomplished in various known ways that enable said connection, for example, through a sewn-in electroconductive filament of steel or other conductive material. In one embodiment of the present invention, the connection is made through a pair of electroconductive filaments 8, 12, which connects the electroactive polymers at both ends of the strip to the first contacts 11 made on the socket 9. In one embodiment, electroconductive filaments 8, 12 may be woven into the elastic material from which the sock 20 is made. The electrical contact between the first contacts 11 on the socket 9 and the second contacts 4 on the sensor-control unit 6 is made in known ways, for example through spring pins. Each individual stretch-measuring sensor 10, i.e. for each individual strip, requires one separate contact, whereas the other contact may be common to multiple sensors. A minimum of four pins are therefore required for a three-strip version.

In the area of attachment of the sensor-control unit 6 to the sock 20, the sock 20 has a hole 7 in order to allow direct contact of the photoplethysmographic sensor with the skin of the person. The photoplethysmographic sensor directly measures heart rate and oxygen saturation of the blood, wherein the sensor must be in direct contact with the skin of the person so that measurements can be made. Further processing of the data obtained through the photoplethysmographic sensor enables, among other things, calculating the blood pressure and displaying the shape of the pulse waves.

For attaching the detachable sensor-control unit 6 to the sock 20 and for the precise positioning of the sensor-control unit 6 on the sock 20 that is necessary for establishing a connection between the first contacts 11 made on the socket 9 and the second contacts 4 made on the sensor-control unit 6 and for inserting the photoplethysmographic sensor into the hole 7, the sock 20 is in the area of attachment of the sensor-control unit 6 to the sock 20, i.e. in the area of the hole 7, provided with a socket 9 into which the sensor-control unit 6 is inserted. The socket 9 is implemented on the sock 20 in such a way that the hole 7 is essentially located in the middle of the socket 9.

The socket 9 and the housing 1 of the sensor-control unit 6 may be implemented in known ways, so as to allow for the attachment, the precise positioning and fixing of the detachable sensor-control unit 6 to the socket 9, for example through the guides provided in the socket 9 and in the housing 1 of the sensor-control unit 6, which allows for a form-fitting connection between the guides of the socket 9 and the housing 1, thereby securing the sensor-control unit 6 to the socket 9.

The socket 9 for the sensor-control unit 6 can be made in any position on the sock 20; it is only necessary to ensure that the sensor-control unit 6 is easily attached to and removed from the sock 20 and that, when inserting the sensor-control unit 6 into the socket 9, the stretch-measuring sensor 10 is in contact with the first contacts 11 made in the socket 9 and the second contacts 4 made in the sensor-control unit 6, and that the photoplethysmographic sensor fits into the hole 7.

Figure 3:
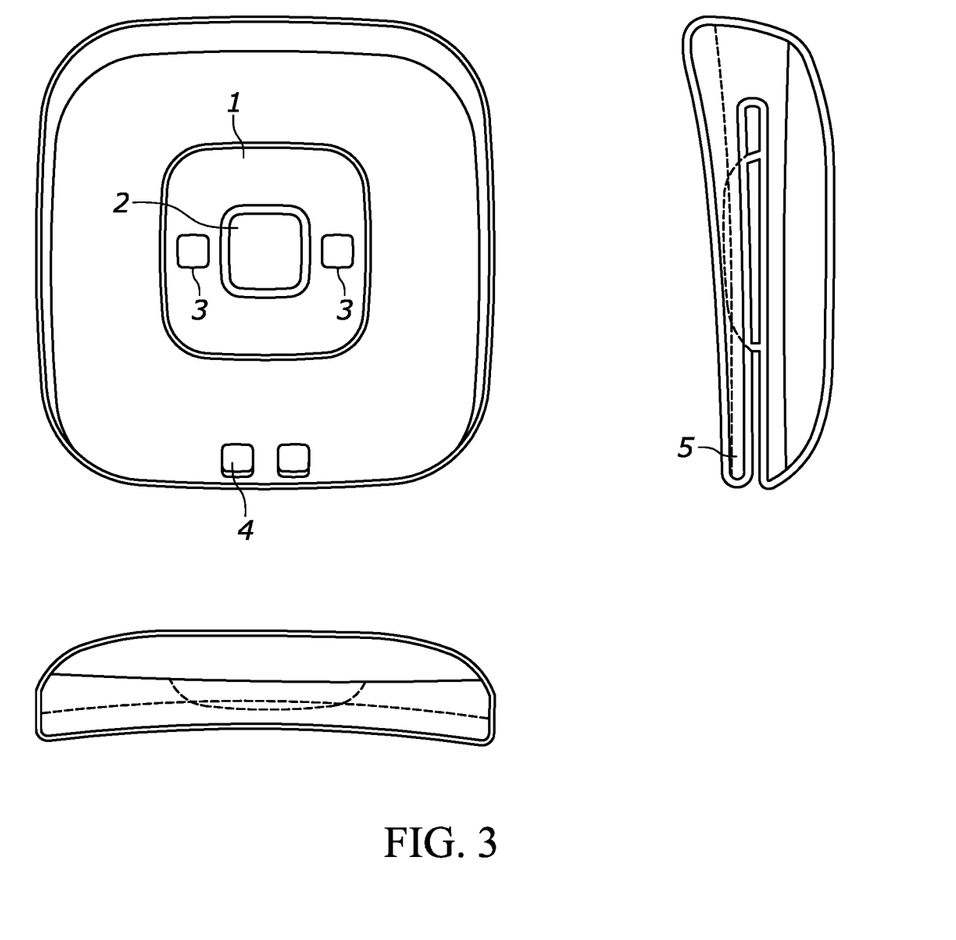
FIG. 3 shows an embodiment of the sensor/control unit in the form of a clip

In one embodiment, this is accomplished by sewing a pocket onto the sock 20 over the socket 9, into which the sensor-control unit 6 is inserted before inserting it into the socket 9. In another embodiment, this is done in such a way that the housing 1 of the sensor-control unit 6 is made in the form of a clip having a corresponding opening in the arm 5 touching the skin of the person, which fits on the hole 7 made in the sock 20, for providing a direct contact between the photoplethysmographic sensor and the skin of the person. The clip is inserted into the notch on the sock 20, which is made above the socket 9, the notch being at such a distance from the socket 9 that direct contact of the photoplethysmographic sensor with the skin of the person is enabled upon insertion of the clip into the notch. In a further embodiment, which is preferred, the socket 9 for the sensor-control unit 6 is made at the upper edge of the sock 20, thus also the hole 7 is provided at the upper edge of the sock 20, and the housing 1 of the sensor-control unit 6 is made in the form of a clip to be fastened to the upper edge of the sock 20, where the socket 9 for the sensor-control unit 6 is provided.

The sensor-control unit 6 is made up of the housing 1, which is shock and scratch resistant and preferably made of plastic or rubberised materials. The sensor-control unit 6, in addition to the above elements, i.e. the second contacts 4 for connection with the first contacts 11 made on the socket 9, the motion sensor, the photoplethysmographic sensor and the temperature sensor, includes the following electronic components:
- a processing unit with a clock,
- a memory unit,
- a communication circuit for wireless communication between the sensor-control unit and an external device, preferably for Bluetooth communication,
- a power supply unit, which is either a battery or an accumulator, and
- other electronic components that are necessary for the normal operation and interconnection of the components of the sensor-control unit 6 and the stretch-measuring sensor 10.

In the case where electroactive polymers are used for the stretch-measuring sensor 10, the sensor-control unit also includes a capacitance-measuring circuit.

Preferably, the motion sensor is a module with a triaxial accelerometer and a triaxial gyroscope. The accelerometer measures and transmits data on the number of steps taken during the day, the distance walked in the day, the dynamics of the movement, detects falls, i.e. whether the person wearing the compression sock walks, runs, or walks the stairs. The gyroscope identifies and transmits data on the detected motion or while laying down, the orientation in space; therefore, the accelerometer and gyroscope provide data on the activity of the person wearing the compression sock according to the invention.

Preferably, the photoplethysmographic sensor comprises two LEDs 3, namely a red-coloured LED and an infra-red LED, along with a phototransistor 2 with maximum sensitivity to red and infra-red wavelengths. The photoplethysmographic sensor measures and transmits data on heart rate and blood oxygen saturation level.

The sensor-control unit 6 may additionally include indicators for displaying the battery status and the ON/OFF status of the sensor-control unit 6. Preferably, the indicator is an RGB LED diode.

The sensor-control unit 6 records, processes and stores the following data through the processing unit and the memory unit along with the time:
- by the sensor for measuring the stretch of the electroactive polymer filament changes in the stretch of the sock resulting from the use of the sock or from the variation in the circumference of the user's leg, such as swelling of the leg are measured;
- by the accelerometer data on the number of steps taken during the day, the distance walked in the day, the dynamics of the movement, detects falls, i.e. whether the person wearing the compression sock walks, runs, or walks the stairs are measured, calculated and transmitted;
- by the gyroscope data on the detected motion or while laying down, the orientation in space are identified and transmitted; therefore, the accelerometer and the gyroscope provide data on the activity of the person wearing the compression sock according to the invention;
- by the photoplethysmographic sensor data on heart rate and blood oxygen saturation level are measured and transmitted;
- by the temperature sensor data on the user's body temperature are measured and transmitted.

The sensor-control unit 6 processes the data obtained from the sensors or by calculation in real time and saves it to the local memory, or transmits it simultaneously or occasionally through the communication unit to an external device, such as a smart phone or a tablet computer equipped with an application that enables the data to be monitored, stored, processed or forwarded, e.g. to a doctor.

The stretch-measuring sensor 10 detects any stretch of the sock 20 caused by wearing or leg swelling. The user's use of the sock can be inferred based on this stretch. In addition, based on the stretch and the dimensions of the sock 20 (especially the sock radius in the horizontal plane), it is possible to infer the pressure of the sock 20 on the user's leg, either by using tables containing data that were previously experientially acquired or by a real-time arithmetic operation based on a pre-set mathematical model, or a combination of both methods. Deduction of the pressure of the sock 20 on the leg of the person based on the detected stretch can be accomplished in real time by the processing unit in the sensor-control unit 6 and the calculated values stored in the memory unit in the sensor-control unit 6 for subsequent transmission to other devices or simultaneous transmission through the circuit for wireless communication.

The tables include, for example, calibration tables of stretch-dependent change in capacitance for each type of sock and calibration tables of stretch-dependent change in degree of compression for each type of sock based on sensor geometry and sensor location.

In the embodiment where a strip of electroactive polymers is used for the stretch-measuring sensor 10, the stretch of the sensor causes a change in capacitance. The electroactive polymer is coupled to the sensor-control unit 6, which measures the capacitance and the change in capacitance of the electroactive polymer, and, based on the calculation, assigns to it an appropriate stretch value. The calculation of the stretch based on the change in capacitance is carried out by the processing unit in the sensor-control unit 6, either through tables containing data that were previously experientially acquired and pre-loaded into the memory of the processing unit, wherein the tables contain capacitance values and other parameters affecting the stretch, e.g. the type and shape of the sock, the position of the sensor and the corresponding stretch value, or through a pre-set mathematical model, or a combination of both methods.

Figure 4:
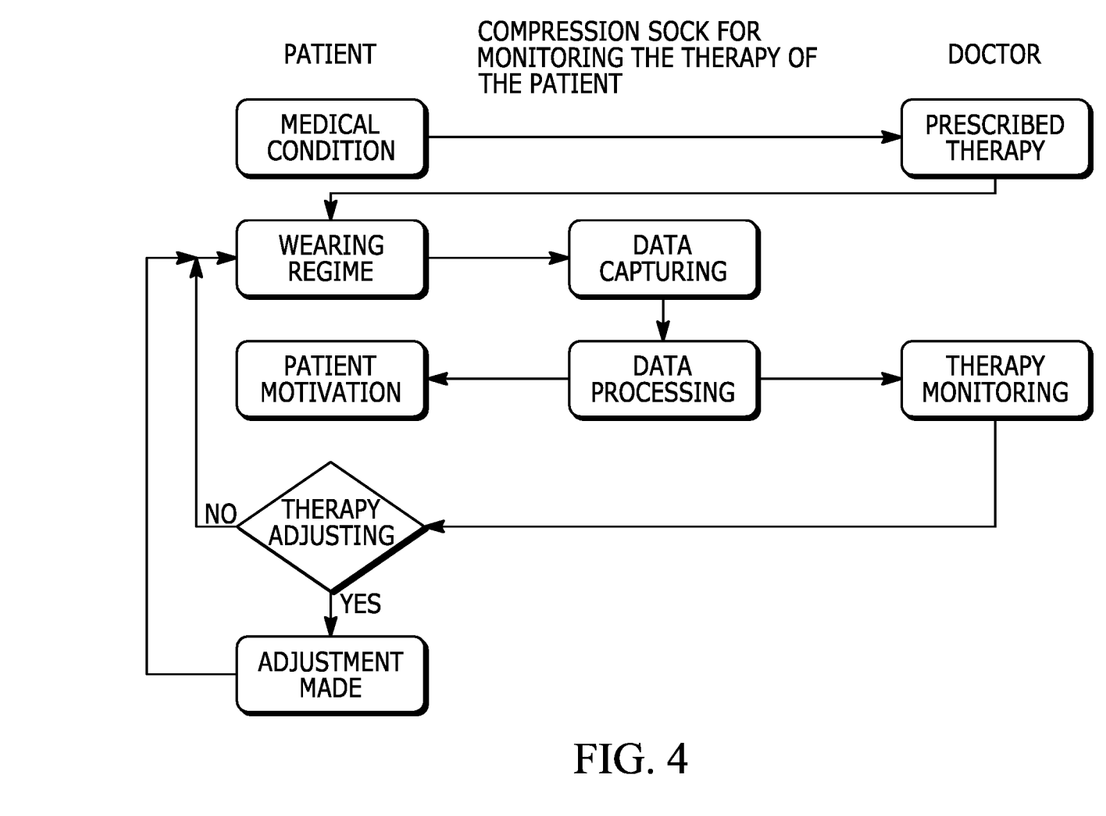

FIG. 4 shows a practical embodiment of the invention. A patient diagnosed with venous insufficiency is prescribed appropriate therapy by a doctor—namely, the doctor determines at least the size of the compression sock, the degree of compression and the wearing regimen. While the patient is wearing the sock, the sensor-control unit captures the data, processes it appropriately and saves it to the memory unit that sends data to a server through a connection to a smart device from which the doctor can obtain it. Based on the data obtained, the doctor monitors the therapy and adjusts it accordingly. During the course of therapy, the patient can monitor his/her activity and vital signs based on data processed through an application on a mobile device, i.e. a phone or a tablet, and thus be motivated to follow the compression garment therapy in the form of gamification.

In one of the embodiments, each sock has its own identification code, which the sensor unit recognizes after insertion into the socket. Based on this, the sensor unit can obtain data about the type of sock—each type of sock can have different characteristics such as size, degree of compression, production date and batch—and the identity of the person, which allows for one sensor unit to be used on several types of socks and for multiple users. The identification code is preferably stored in the socket and is readable by the sensor unit in known ways, e.g. through a read-only memory built into the socket. Identification can also be made through an application on a smart device, e.g. a smart phone, into which the user enters the identification code or the phone reads it from a bar code, a QR code or an NFC chip.

The invention claimed is:

1. A tubular compression sock for monitoring therapy and physiological activity of a person, said tubular compression sock comprising:
a sensor-control unit;
at least two stretch-measuring sensors attached to the tubular compression sock between a knee and an ankle area;
wherein the at least two stretch-measuring sensors are implemented as a strip made of electroactive polymers that change capacitance during stretch, and the at least two stretch-measuring sensors are attached to the tubular compression sock, the strip made of electroactive polymers substantially circumscribing a part of a body, and to measures how a circumference of the part of the body changes in a circumferential direction perpendicular to a longitudinal axis of the part of the body wrapped by the tubular compression sock;
wherein the tubular compression sock is provided with a socket for receiving the sensor-control unit, the socket provided with first contacts for connection with the at least two stretch-measuring sensors and the tubular compression sock in an area of the socket, provided with a hole;
wherein the sensor-control unit is provided with second contacts to connect to the first contacts on the socket;
and wherein the sensor-control unit comprises at least one of a motion sensor, a photoplethysmographic sensor, a temperature sensor and a processing unit with a clock, the sensor-control unit being detachably secured to the tubular compression sock.

2. The tubular compression sock according to claim 1, wherein a length of the strip of electroactive polymers is at least equal to one third of a circumference of the tubular compression sock at an attachment point of the at least two stretch-measuring sensors and, at a maximum, a distance between both ends of the at least two stretch-measuring sensors is 5 mm.

3. The tubular compression sock according to claim 1, wherein a connection of the at least two stretch-measuring sensors, at both ends of the strip of electroactive polymers, with the first contacts made on the socket is made through a pair of electroconductive filaments, which connects the electroactive polymers at both ends of the strip to the first contacts made on the socket, and the pair of electroconductive filaments are woven into an elastic material of which the tubular compression sock is made.

4. The tubular compression sock according to claim 1, characterized in that an electrical contact between the first contacts made on the socket and the second contacts made on the sensor-control unit is made through spring pins, wherein each of the at least one single stretch-measuring sensor utilizes one separate contact, whereas another contact is common to multiple sensors.

5. The tubular compression sock according to claim 1, wherein the socket on the tubular compression sock is implemented to locate the hole substantially in a middle of the socket.

6. The tubular compression sock according to claim 1, wherein the sensor-control unit is made up of a housing in a form of a clip, wherein the clip has, in an arm touching a skin of the person, an opening which fits on the hole made in the tubular compression sock, for providing a direct contact between the photoplethysmographic sensor and the skin of the person.

7. The tubular compression sock according to claim 1, wherein the socket and a housing of the sensor-control unit are provided with guides for a form-fitting connection between the guides of the socket and the housing for positioning and fixing of the sensor-control unit to the socket.

8. The tubular compression sock according to claim 1, wherein the sensor-control unit further comprises a capacitance-measuring circuit, a memory unit, a communication circuit for wireless communication between the sensor-control unit and an external device, and a power supply unit, for operation and interconnection of the sensor-control unit and the at least two stretch-measuring sensors.

9. The tubular compression sock according to claim 1, wherein the sensor-control unit processes data obtained from at least one of the at least two stretch-measuring sensors and by a real-time calculation, and at least one of saves the data to a local memory and transmits the data one of simultaneously and occasionally through a communication unit to an external device equipped for at least one of monitoring, storing, processing and forwarding the data.

10. The tubular compression sock according to claim 1, wherein the socket for the sensor-control unit is made at an upper edge of the tubular compression sock, and the hole is made at the upper edge of the tubular compression sock.

11. The tubular compression sock according to claim 1, wherein the at least two stretch-measuring sensors include a first stretch-measuring sensor disposed in an upper region of a calf below the knee, a second stretch-measuring sensor disposed approximately in a middle of a calf area, and a third stretch-measuring sensor disposed in the ankle area.

* * * * *